United States Patent [19]

Hayashi et al.

[11] Patent Number: 4,783,419

[45] Date of Patent: Nov. 8, 1988

[54] EXAMINING CELLS BY ELECTROPHORESIS

[75] Inventors: Haruhisa Hayashi; Yoshiharu Oguchi; Kenichi Matsunaga, all of Tokyo; Chikao Yoshikumi, Kunitachi, all of Japan

[73] Assignee: Kureha Kagaku Kogyo Kabushiki Kaisha, Tokyo, Japan

[21] Appl. No.: 714,453

[22] Filed: Mar. 21, 1985

[30] Foreign Application Priority Data

Mar. 30, 1984 [JP] Japan .................................. 59-62446

[51] Int. Cl.$^4$ .................. G01N 33/554; G01N 33/561
[52] U.S. Cl. .................. 436/516; 204/183.3; 204/299 R; 435/29; 436/506; 436/519; 436/520; 436/548; 436/806; 436/811; 436/813
[58] Field of Search ........................ 204/183.3, 299 R; 435/29; 436/516, 519, 520, 806, 506, 548, 813, 811

[56] References Cited

U.S. PATENT DOCUMENTS 3,984,533 10/1976 Uzgiris ............................ 204/299 R
4,011,044 8/1977 Uzgiris ............................ 23/230 B

FOREIGN PATENT DOCUMENTS 0070153 1/1983 European Pat. Off. .
2007716 5/1979 United Kingdom .

OTHER PUBLICATIONS

A. S. G. Curtis, *The Cell Surface,* Academic Press, New York, 1967, p. 16.
E. Hansen et al., *Journ. Immunol. Meth.,* 51, 197–208, 1982.
E. Hansen et al., *Meth. Enzymol,* 108, 180–197, 1984.
Laitinen, *Chemical Analysis,* McGraw-Hill Book Company, Inc., New York, 1960, p. 9.

*Primary Examiner*—Robert J. Warden
*Assistant Examiner*—David A. Saunders
*Attorney, Agent, or Firm*—Oblon, Fisher, Spivak, McClelland & Maier

[57] ABSTRACT

Disclosed herein is a method for examining cells, comprising subjecting the cells to an antigen-antibody reaction treatment, then measuring a pattern of the electrophoretic mobility of the cells and comparing the electrophoretic property of the cells under examination with the electrophoretic property of standard cells.

15 Claims, 7 Drawing Sheets

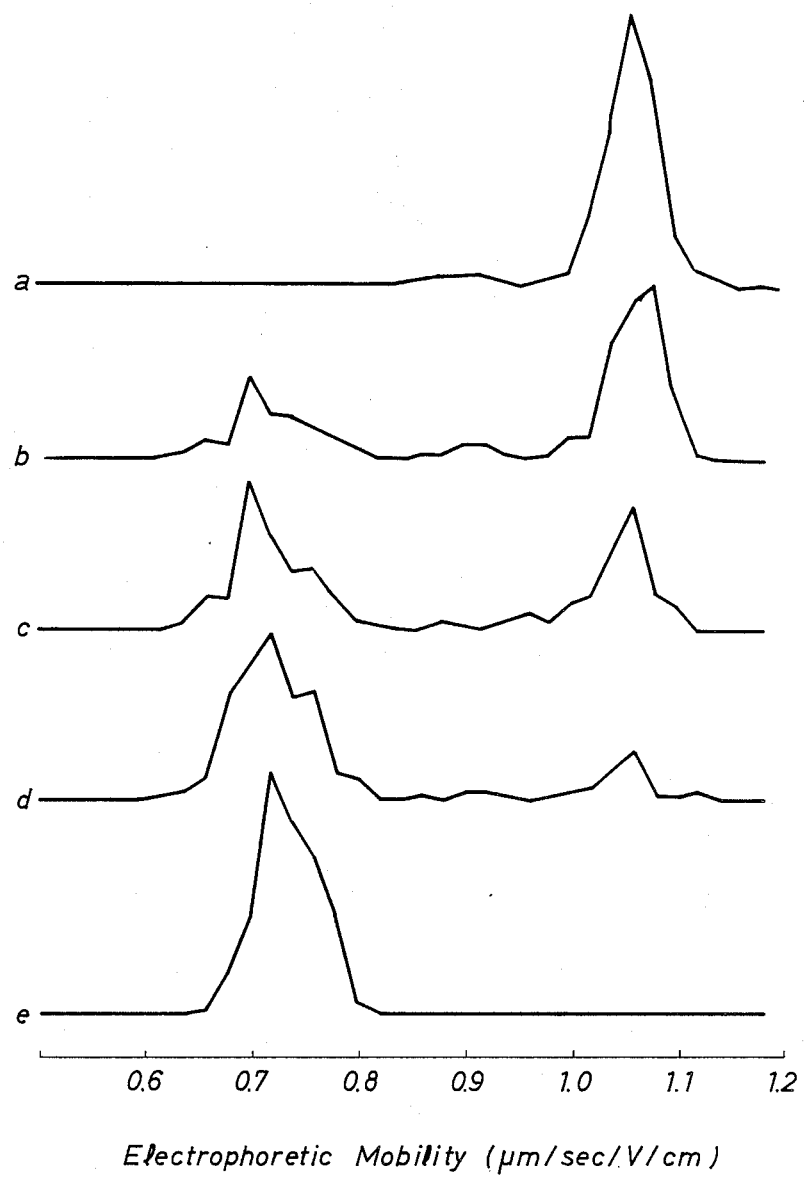

Electrophoretic Mobility ( µm/sec/V/cm )

EXAMINING CELLS BY ELECTROPHORESIS

BACKGROUND OF THE INVENTION

1. Field of the Invention

This invention relates to a method for examining a cell by subjecting the cells to an antigen-antibody reaction treatment, then measuring the electrophoretic mobility of the cells by an automatic cell-electrophoresis apparatus to obtain an electrophoretic mobility pattern and comparing the electrophoretic property of the cells under examination with the electrophoretic property of cells of a standard. The present invention also relates to a method for measuring the antibody or the antigen on the cell membrane from the change in properties concomitant with the change of surface charges of the cell before and after the antigen-antibody reaction treatment.

2. Discussion of the Background

For measuring the antigen of the cell surface, a method has been generally used in which the antibody is labeled with a fluorescent substance such as FITC and RITC, and the fluorescence-labeled cells and unlabeled cells are discriminated visually under a fluorescence microscope, or such determination method has been conducted by an automatic apparatus using laser beams such as flow cytometer.

The conventional method using a fluorescence microscope, however, requires skill and complicated operations. It is also time-consuming and further there is the problem in accuracy of measurement because of the dependence on the visual observation. On the other hand, the automatic apparatuses such as flow cytometry and FACS are very elaborate and large-scaled, and require great cost and scrupulous care for their maintenance.

Radioimmunoassays and enzymimmunoassays are high in sensitivity and capable of microanalysis, but these methods, as in the case of fluoroimmunoassay, require the use of a labeled antibody, and since such labeled antibody undergoes a change with time, the preservation of the labeled antibody is difficult. Further, these methods are a time-consuming in a process for pretreatment which requires skill, and further, a specific apparatus must be used for conducting the measurement. Especially radioimmunoassay is attended with danger because of the use of a radioisotope and is also subject to various restrictions in its practice such as the necessity of a specific facility for the treatment of radioisotope.

The object of the present invention is to provide a method for examining cells, which is free of the defects of the conventional methods and which is easy and quick to practice, high in precision and safe in operation.

By the way, cell-electrophoresis is attracting attention as a useful means for examining cellular immunity, and it has been reported that this method can be an effective examination means not only for animals but also for man by analyzing the change of electrophoretic pattern of lymphocytes (refer to Japanese Patent Application Laid-Open No. 9060/1983).

SUMMARY OF THE INVENTION

In an aspect of the present invention, there is provided a method for examining cells, which comprises subjecting the cells to an antigen-antibody reaction treatment, measuring a pattern of the electrophoretic mobility of the cells, and comparing the electrophoretic property of the cells under the examination with the electrophoretic property of standard cells.

BRIEF DESCRIPTION OF THE DRAWINGS

FIG. 1, FIGS. 3 to 5, FIG. 7 and FIG. 8 show the electrophoretic patterns according to the method of the present invention.

DETAILED DESCRIPTION OF THE INVENTION

Figure 1:
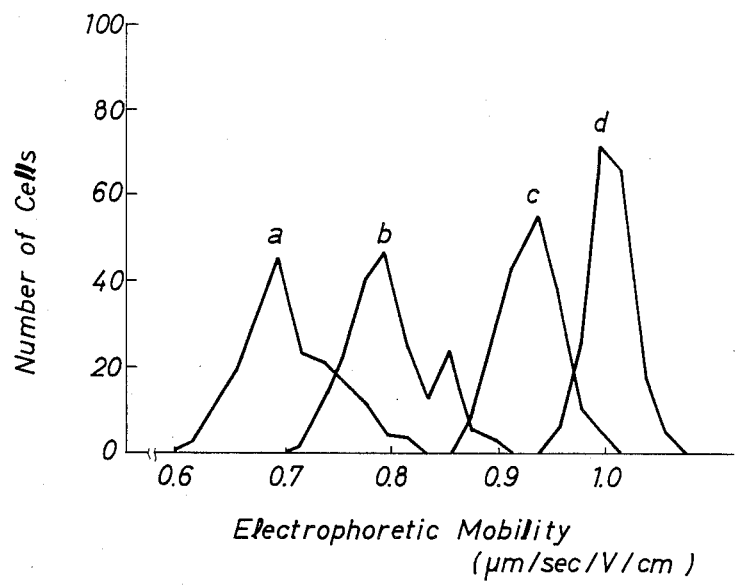

"A cell-electrophoretic method" is a method in which the free cells are washed and then added with an antibody, and after reacting them for a given period of time and further washing, the electrophoretic mobility of the cells is measured by an automatic cell-electrophoresis apparatus. In the case where the change of mobility of a reaction antibody (primary antibody) of the objective antigen is too small, by using a reaction antibody product (secondary antibody) of such primary antibody or a reaction antibody product (tertiary antibody) of the secondary antibody, a more definite change can be obtained. In such measurement of electrophoretic mobility, it is not intended to merely measure the average mobility. It is essential to measure the mobility of many cells in a short time while making automatic recording of a histogram pattern and to analyze such pattern.

When making cell-electrophoretic measurement measurements using conventional techniques, it is difficult to make measurements of many cells in a short time when the cells make no change yet, and the accuracy of measurement is also low.

The method of the present invention is to measure the electrophoretic mobility of the cells by an electrophoretic method with extremely high separability, and from the change of the measured electrophoretic mobility pattern, it is possible to obtain information unobtainable with the conventional methods.

The method of the present invention has the following technical advantages:

(1) A large number of cells can be analyzed in a short time.

(2) The accuracy of measurement is high since the average electrophoretic mobility of the individual cells can be measured by inverting the electric field.

(3). The minute suspended materials such as platelets, contaminants, etc., and the agglomerated cells are not measured.

(4) It is possible to use a medium of physiological conditions (ionic strength $I=0.15$ moles/l) as the cell suspension for electrophoresis.

Regarding (4) in particular, the research reports show that the measurements have been conducted mostly under the conditions (ionic strength $I=0.005-0.1$) lower than the physiological conditions as a result of lowering the electrical conductivity of the cell suspension due to the problems over apparatus and determination techniques, but from the point of view of measuring the live cells, it is desirable to use a cell suspension which meets physiological conditions.

The automatic electrophoresis apparatus (Parmoquant: made by VEB CARL ZEISS JENA, or KUREHA CHEMICAL INDUSTRY CO., LTD.) used in the Examples shown below is capable of correctly measuring the average electrophoretic mobility of each of a great many of cells by inversion of the electric field, and the measurements are processed into a histogram for mobility. In this case, for the reasons relating to the image treatment, it is desirable to adjust the cell concentration of the specimen in the range of 0.5 to $20 \times 10^6$ cells/ml and the ionic strength of the cell suspension in the range of 0.11 to 0.21 moles/l, preferably 0.13 to 0.17 moles/l.

The measuring apparatus usable in the present invention, however, is not limited to the automatic electrophoresis apparatus and it is possible to employ other measuring devices that can satisfy the above-mentioned conditions, for instance the devices using Laser Doppler method, Laser Grating method or Free Flowing method.

The antibodies usable in the present invention include all types of antibodies to the antigens existing on the cell membrane. It is possible to use not only polyclonal antibodies obtainable from the immunized animals such as rabbit, goat, mouse, horse, sheep, chicken, ape, etc., but also monoclonal antibodies obtained from cell fusion. Man's antibodies can be also used. The method of the present invention can be applied to the measurement of red blood cells, white blood cells, myeloma cells, cancer cells and various affected cells, and is especially useful for the measurement of subsets of lymphocytes and macrophages where a number of antibodies are produced. It is thus possible to measure even the constructional ratio of particular cells by adding an antibody specific to such cells, measuring the patterns before and after the reaction by the method of the present invention and analyzing such patterns.

It is further possible with the method of the present invention to detect the difference between normal cell and affected cell or to detect the change of a cell with the progress of the disease, especially the cell condition in the initial stage of the disease.

As explained above, the method of the present invention is useful for the examination of various kinds of affected cells such as tumor cells and the cells affected by such diseases as bronchial asthma, multiple sclerosis, diseases of the nervous system, diseases of the thyroid gland, autoimmune diseases, etc. The present method can be also used for the differentiation of immunity.

As apparent from the foregoing description, the method of the present invention is very simple, very effective and accurate measurement method of cells.

The present invention will be described in further detail below by way of the embodiments thereof.

EXAMPLE 1

The sheep red blood cells (hereinafter abbreviated as SRBC) obtained from the preserved blood of sheep (supplied from Japan Bio-Material Center Co., Ltd.) were subjected twice to centrifugal washing with a Hanks' balanced salt solution (hereinafter abbreviated as HBSS).

As the antibody, the supernatant of ascites obtained by transplanting the anti-SRBC monoclonal antibody (hereinafter abbreviated as anti-SRBC·Mc Ab) producing cells prepared in the usual way into the abdominal cavity of mouse was used. Normal mouse serum was used as control.

Figure 2:
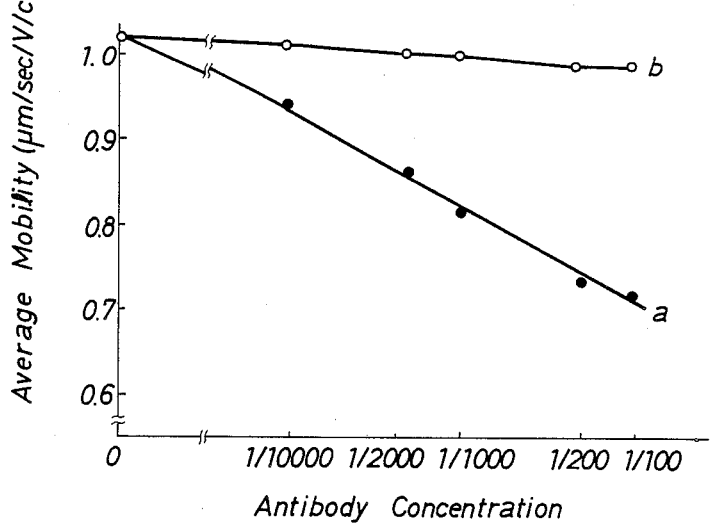
FIG. 2 is a graph showing the relation between antibody concentration and average electrophoretic mobility.

The washed SRBC were combined with anti-SRBC·Mc Ab or control serum and the mixture allowed to react at 4° C. for 30 minutes and, after additional washing, the reaction mixture was subjected to electrophoresis by an automatic electrophoresis apparatus (Parmoquant: made by Kureha Chemical Industry Co., Ltd.). The results are shown in FIG. 1 and FIG. 2. In FIG. 1, letters a, b, c and d represent the results obtained at antibody concentrations of 1/100, 1/1000, 1/10000 and 0, respectively. As shown in FIG. 1, the electrophoretic histogram pattern of SRBC shifted to the lower mobility side with increase of antibody concentration. The average mobility also lowered proportionally to antibody concentration in the case of (a) where anti-SRBC·Mc Ab was added, as shown in FIG. 2. On the contrary, control serum (b) showed almost no change of mobility by antibody concentration.

EXAMPLE 2

SRBC was obtained from the preserved blood of sheep (supplied from Japan Bio-Material Center Co., Ltd.) and mouse red blood cell (hereinafter abbreviated as MRBC) from the peripheral blood of ICR mouse, and SRBC and MRBC were respectively subjected twice to centrifugal washing with HBSS, followed by the measurement of the number of the cells. Both SRBC and MRBC were adjusted to a cell concentration of $1 \times 10^7$ cells/ml, and the suspensions of SRBC and MRBC were mixed in the ratio of 1:1. To the mixed suspension was added anti-SRBC·Mc Ab in a ratio of 100 $\mu$l to 1 ml of the suspension, and the mixture was reacted at 4° C. for 30 minutes. The reaction mixture was then washed twice with a culture medium (Eagle's MEM) and then the electrophoretic mobility pattern was measured by an automatic electrophoresis apparatus (Parmoquant, made by Kureha Chemical Industry Co., Ltd.). The electrophoresis was conducted at a current of 12.5 mA and a temperature of 24° C.

Figure 3:
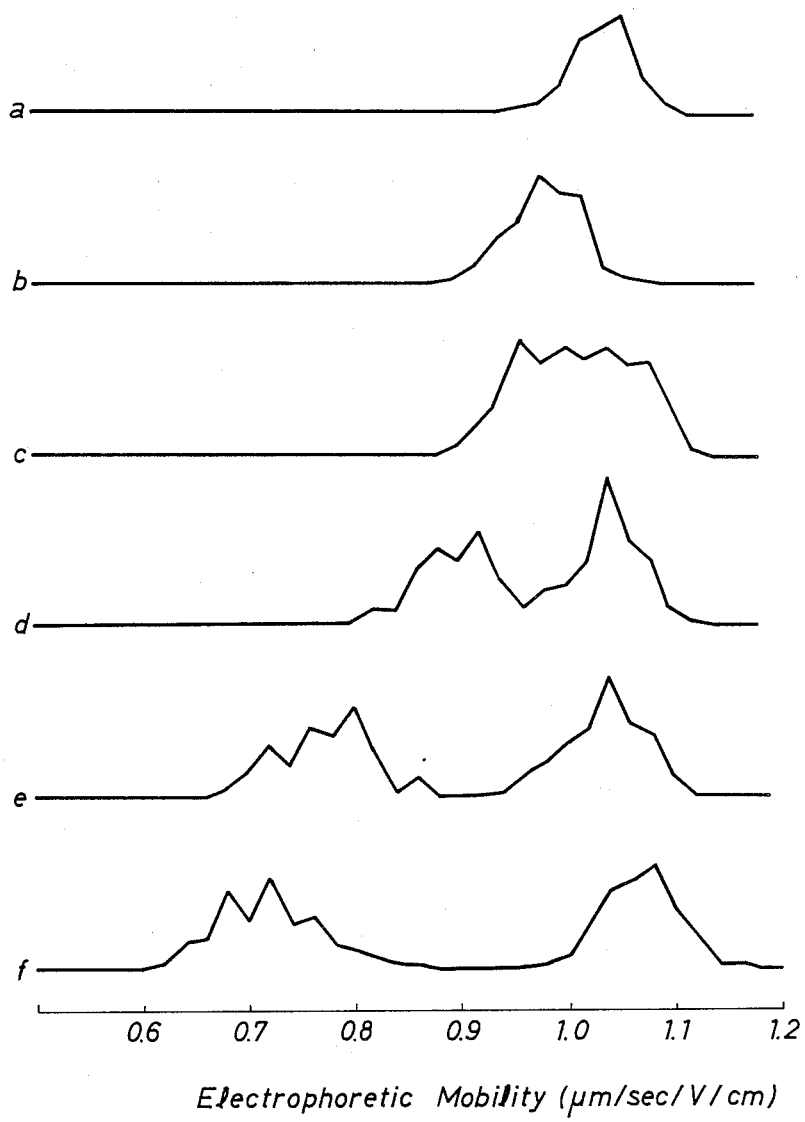

Similar measurements were conducted on the specimens prepared by reacting 1:1 mixture of SRBC and MRBC with anti-SRBC·Mc Ab of various concentrations. The obtained results are shown in FIG. 3. As seen from FIG. 3, single MRBC (a) and single SRBC (b) showed the mobility patterns which resembled each other, but the mixture thereof (c) showed a pattern having a broad peak. When anti-SRBC·Mc Ab was added to this mixed system, the peak of SRBC shifted to the low mobility side as the antibody concentration increased (d.=1/10000, e =1/1000, f =1/100), but the peak of MRBC remained substantially unchanged.

EXAMPLE 3

Figure 4:
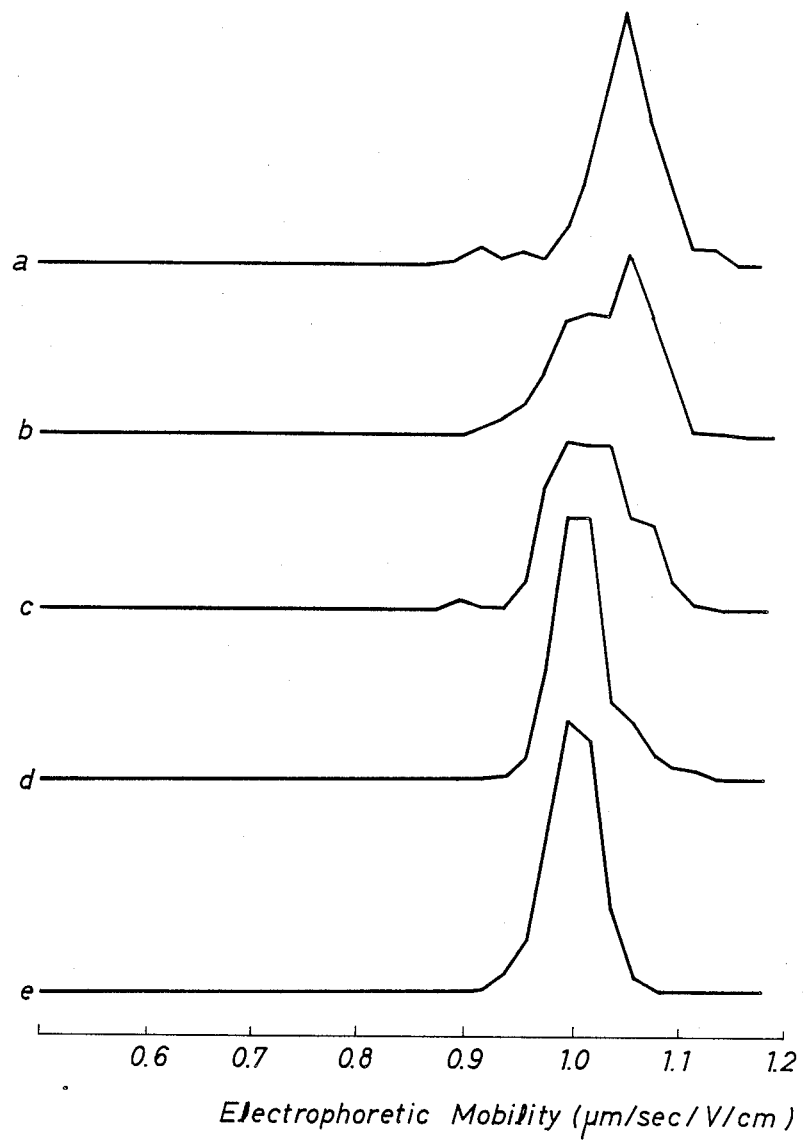

Suspensions of SRBC and MRBC, each with a cell concentration of $1 \times 10^7$ cells/ml, were prepared according to the method of Example 2, and these suspensions were mixed in the SRBC:MRBC ratios of 0:10 (single MRBC,(a)), 2:8 (b), 5:5 (c), 8:2 (d) and 10:0 (single SRBC, (e)). The electrophoretic mobility patterns of SRBC, MRBC and mixtures thereof have a broad peak as shown in FIG. 4, and it is impossible to separate the peak of SRBC and the peak of MRBC.

To each of the cell suspensions was added anti-SRBC·Mc Ab in a ratio of 1/100 for reacting the mixture at 4° C. for 30 minutes, and after washing, the electrophoretic mobility patterns were measured under the same conditions as in Example 2, obtaining the results shown in FIG. 5. As seen from FIG. 5 (in which a to e represent the same as in FIG. 4), the peak of SRBC, shifted to the vicinity of 0.7 μm/sec/V/cm, and the peak size changed in accordance with the cell mixing ratio.

Figure 6A:
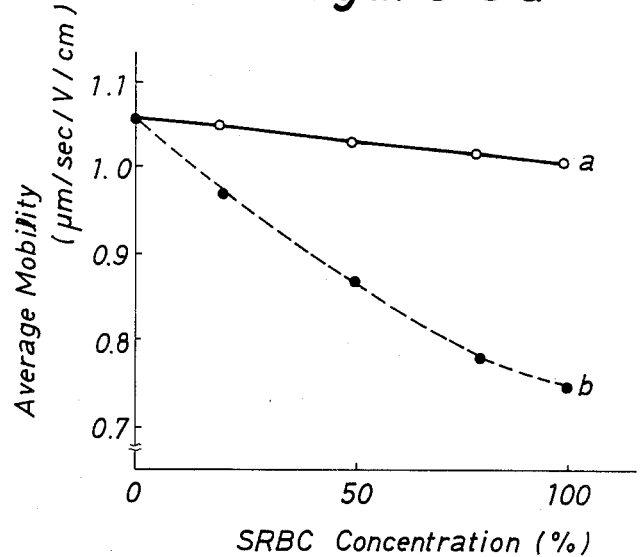
FIG. 6a is a graph showing the relation between mixing ratio of SRBC and average electrophoretic mobility.
Figure 6B:
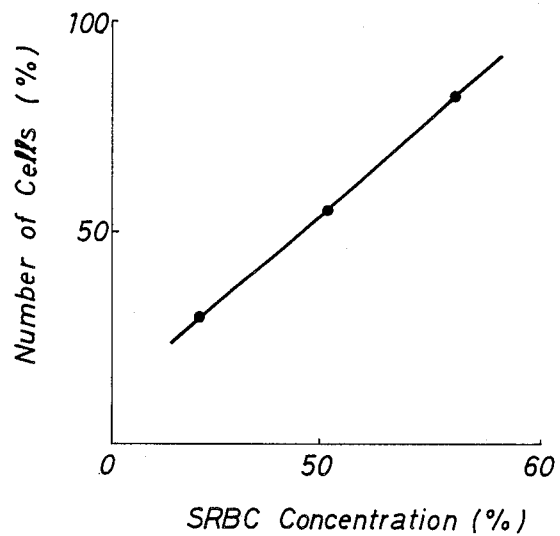
FIG. 6b is a graph showing the relation between mixing ratio of SRBC and number of cells.

FIG. 6a shows the relation between mixing ratio of SRBC and average mobility, while FIG. 6b shows the relation between mixing ratio of SRBC and ratio of the cell group having a peak in the vicinity of 0.7 μm/sec/V/cm as determined from the electrophoretic mobility pattern. Both patterns are substantially in accordance with each other, and this fact certifies that the cell mixing ratio can be measured by the method of the present invention.

In FIG. 6a, a represents the case where no anti-SRBC·Mc Ab was added, and b represents the case where it was added.

EXAMPLE 4

Figure 7:
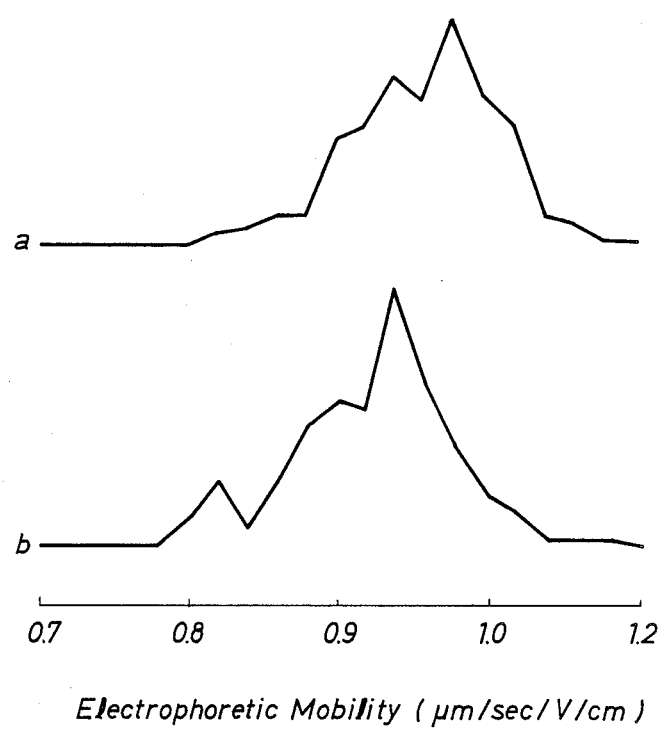

Histiocytic lymphoma cell line U 937 (human macrophage-like cell line) (S. Maruyama et al: Recordings of the General Meeting of Japan Immunological Society, 11,443 (1981)) derived from human macrophage (hereinafter abbreviated as Mϕ) and anti-human macrophage monoclonal antibody (hereinafter abbreviated as anti-Mϕ·Mc Ab) (made by Wako Junyaku Kogyo KK) were used. 1 ml of 10 times diluted anti-Mϕ·Mc Ab was added to histiocytic lymphoma cell line U 937 which has been washed twice with HBSS, and after 30-minute reaction at 4° C., the mixture was washed twice with HBSS and then washed once with Eagle's MEM. The electrophoretic patterns of this specimen and Mϕ were measured with an automatic electrophoresis apparatus (Parmoquant: made by Kureha Chemical Industry Co., Ltd.) under the same conditions as in Example 2. The results are shown in FIG. 7. In the case of (b) where anti-Mϕ·Mc Ab was added, the peak of the pattern shifted to the low mobility side as compared with the case of (a) where no anti-Mϕ·Mc Ab was added.

EXAMPLE 5

0.5 ml of peripheral blood was collected from a normal person and from a patient of autoimmune hemolytic anemia. 0.5 ml of heparin was added to each blood sample and the mixture was washed twice with MEM, added with anti-human IgG antibody (made by MILES-YEDA) in an amount of 280 μg to $5 \times 10^7$ cells/ml and incubated at 25° C. for 20 minutes. Then the reaction mixture was washed once with MEM and subjected to the measurement of electrophoretic mobility in the same way as Example 2. The similar measurement was also made on the specimens to which no anti-human IgG antibody was added.

Figure 8:
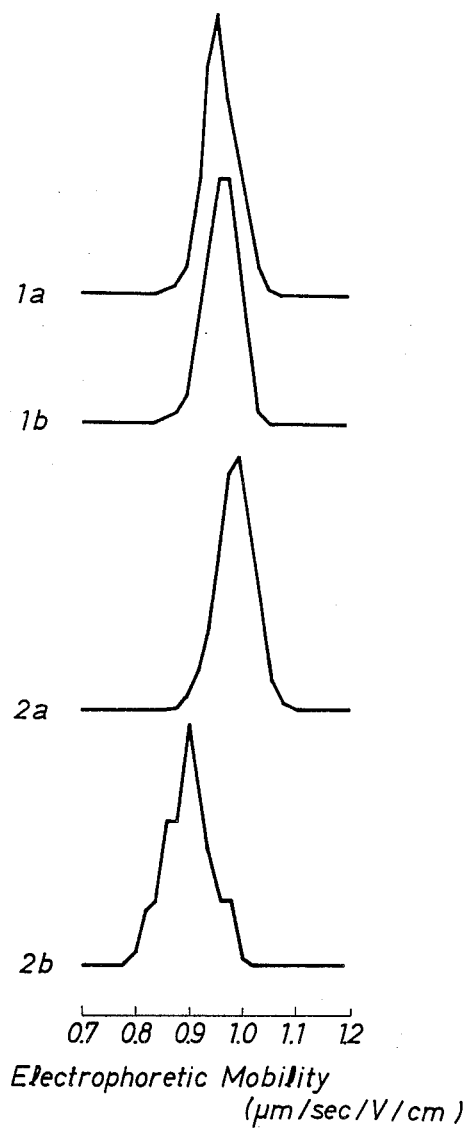

The results are shown in FIG. 8 in which 1 represents the specimens obtained from the normal person and 2 the specimens obtained from the patient of autoimmune hemolytic anemia, and also a represents the case where no antibody was added and b the case where the antibody was added. In the case of the normal person, as indicated by 1 in FIG. 8, the average mobility remained substantially unchanged at about 0.98 μm/sec/V/cm whether the antibody was added or not, but in the case of the patient of hemolytic anemia, as indicated by 2 in FIG. 8, the electrophoretic mobility lowered with the addition of the antibody, showing a 9% decrease of average mobility from 1.00 μm/sec/V/cm to 0.91 μm/sec/V/cm. From this change of mobility pattern, it can be assumed that almost all of the red blood cells of the patient are deposited with the anti-human IgG antibody. For, in case the normal red blood cells exist partly, there will be obtained a pattern which slopes down wider to the high mobility side near 1.0 μm/sec/V/cm.

What is claimed is:

1. A method for examining cells, comprising:
   subjecting specimen cells to an antigen-antibody reaction treatment;
   measuring a pattern of the electrophoretic mobility of the treated specimen cells in a physiological medium having an ionic strength of 0.11 to 0.21 moles/l; and
   comparing the electrophoretic mobility of the treated specimen cells under examination with the electrophoretic mobility of control cells.

2. The method of claim 1, comprising using untreated cells as control cells.

3. The method of claim 1, comprising conducting the electrophoresis measurements with an apparatus capable of automatically measuring the electrophoretic mobility of cells.

4. The method of claim 1, comprising using a concentration of specimen cells in the range of $0.5 \times 10^6$ cell $ml^{-1}$ to $20 \times 10^6$ cell $ml^{-1}$.

5. The method of claim 4, comprising using a medium having an ionic strength of 0.13 to 0.17 moles/l.

6. The method of claim 1, wherein the specimen cells are red blood cells, white blood cells, or cancer cells.

7. The method of claim 1, comprising examining lymphocytes or macrophages.

8. The method of claim 1, wherein the specimen cells are cells suspected of having been affected by a tumor, bronchial asthma, a nervous system disease, or an autoimmune disease.

9. The method of claim 1, comprising measuring the electrophoretic mobility of specimen cells to detected the difference between normal cells and cells affected with a disease to detect a change in the disease.

10. The method of claim 1, wherein the specimen cells are cells suspected of having been affected by a change in the immune status of a patient.

11. The method of claim 1, comprising reacting the specimen cells with an antibody.

12. The method of claim 11, wherein the antibody is a monoclonal antibody obtained from hybrid cells prepared by cell fusion.

13. The method of claim 11, wherein the antibody is a human antibody.

14. The method of claim 11, wherein the antibody is a polyclonal antibody.

15. The method of claim 14, wherein the polyclonal antibody is obtained from an immunized rabbit, goat, mouse, horse, sheep, chicken, or ape.

* * * * *